(12) United States Patent
Papac et al.

(10) Patent No.: US 10,842,573 B2
(45) Date of Patent: Nov. 24, 2020

(54) PREDICTIVE APPARATUS FOR ASSISTING A PHYSICIAN DURING OPHTHALMIC SURGERY

(71) Applicant: Novartis AG, Basel (CH)

(72) Inventors: Michael J. Papac, North Tustin, CA (US); Robert Joseph Sanchez, Jr., Oceanside, CA (US)

(73) Assignee: Alcon Inc. (CH)

(*) Notice: Subject to any disclaimer, the term of this patent is extended or adjusted under 35 U.S.C. 154(b) by 578 days.

(21) Appl. No.: 15/245,328

(22) Filed: Aug. 24, 2016

(65) Prior Publication Data

US 2018/0055581 A1 Mar. 1, 2018

(51) Int. Cl.
| | |
|---|---|
| A61B 34/00 | (2016.01) |
| G06F 19/00 | (2018.01) |
| G16H 50/50 | (2018.01) |
| A61B 3/10 | (2006.01) |
| A61B 8/10 | (2006.01) |
| A61F 9/007 | (2006.01) |
| A61B 34/20 | (2016.01) |
| A61F 9/008 | (2006.01) |

(52) U.S. Cl.
CPC ............. *A61B 34/25* (2016.02); *A61B 3/102* (2013.01); *A61B 8/10* (2013.01); *A61F 9/00736* (2013.01); *G06F 19/321* (2013.01); *G16H 50/50* (2018.01); *A61B 2034/2065* (2016.02); *A61B 2034/252* (2016.02); *A61F 2009/00851* (2013.01)

(58) Field of Classification Search
CPC ........... A61B 34/25; A61B 8/10; A61B 3/102; A61B 2034/2065; A61B 2034/252; G16H 50/50; G06F 19/321; G06F 19/00; A61F 9/00736; A61F 2009/00851
See application file for complete search history.

(56) References Cited

U.S. PATENT DOCUMENTS

| | | | | |
|---|---|---|---|---|
| 6,458,120 B1* | 10/2002 | Shen | ................... | A61F 9/00814 606/10 |
| 7,192,412 B1* | 3/2007 | Zhou | ................... | A61F 9/00781 604/8 |

(Continued)

FOREIGN PATENT DOCUMENTS

| | | |
|---|---|---|
| WO | 94/18636 A2 | 8/1994 |
| WO | 2016/082017 A1 | 6/2016 |

OTHER PUBLICATIONS

Van Beurden, et al., "Effectiveness of stereoscopic displays in medicine: a review" (2012). 3D Research, 3(1), pp. 1-13 (Year: 2012).*

*Primary Examiner* — Oommen Jacob
(74) *Attorney, Agent, or Firm* — Joseph Weatherbee, Esq.

(57) ABSTRACT

A method and system assist a physician in performing an ophthalmic surgery. The method includes receiving a quasi-real time image of at least a first portion of the eye. The at least the first portion of the eye includes an operating field for the ophthalmic surgery. A recommended next region and a recommended next procedure are determined based on the quasi-real time image and a computational model of the eye. An expected next result for the recommended next procedure is calculated using the quasi-real time image and the computational model. The recommended next region, the recommended next procedure and the expected result are provided to the physician.

16 Claims, 5 Drawing Sheets

(56) References Cited

U.S. PATENT DOCUMENTS

| | | | |
|---|---|---|---|
| 2008/0082088 A1* | 4/2008 | Kurtz | A61F 2/142 606/5 |
| 2008/0086048 A1* | 4/2008 | Dupps, Jr. | A61B 3/10 600/405 |
| 2008/0206149 A1* | 8/2008 | Haritoglou | A61K 49/0021 424/9.6 |
| 2010/0049447 A1 | 2/2010 | Peyman et al. | |
| 2010/0256965 A1 | 10/2010 | Rathjen | |
| 2012/0133890 A1* | 5/2012 | Rathjen | A61B 3/024 351/209 |
| 2014/0098346 A1* | 4/2014 | Rathjen | A61B 3/107 351/212 |
| 2015/0031993 A1* | 1/2015 | Buckland | A61B 3/102 600/425 |
| 2016/0192835 A1* | 7/2016 | Matz | A61B 3/13 351/206 |
| 2017/0181626 A1* | 6/2017 | Shau | A61B 3/0025 |

* cited by examiner

PREDICTIVE APPARATUS FOR ASSISTING A PHYSICIAN DURING OPHTHALMIC SURGERY

BACKGROUND

The human eye sees by transmitting and refracting light through a clear outer portion of the eye called the cornea, focusing the light via a lens, transmitting the focused light through the vitreal cavity and onto the retina. The quality of the focused image depends on many factors including but not limited to the size, shape and length of the eye, the quality of the vitreous humor, and the shape and transparency of the cornea and lens. Trauma, age, disease and/or another malady may cause an individual's vision to degrade. The treatment for such conditions includes ophthalmic surgery.

For example, changes in the vitreous cavity, either spontaneous or due to disease, may cause epiretinal membrane (ERM) growth within the vitreous cavity. The ERM may adversely affect vision and pull on the retina. The retina may pucker and eventually tear. In order to address this, ophthalmic surgery may be performed to remove the ERM.

In order to perform an ERM removal, a physician may perform a fundus exam by dilating and examining the eye. The physician may also photograph or create a drawing of the eye during the exam. Surgery may then be scheduled. The physician may prepare a surgical plan based on the photograph and clinical notes from the exam. The surgical plan indicates where in the vitreal cavity the ERM was present during the exam and may note likely positions at which cuts can be made to the ERM for removal. The physician may start the surgery based in part on the surgical plan, and proceed based on the current status of the patient.

Although the ophthalmic surgery may be performed, the status of the eye may have changed significantly between the time of the last clinical exam and the surgery. For example, for diabetic retinopathy, there can be substantial progression of the disease in the time between the last exam and the surgery. As a result, the physician may need to make changes to the surgical plan on the fly. In addition, the situation presented to the physician may be very complex. Consequently, the starting point for the ERM removal or other procedure and/or the next step in the procedure may be difficult to determine.

Accordingly, what is needed is a mechanism for assisting a physician in planning and carrying out surgery.

BRIEF SUMMARY OF THE INVENTION

A method and system assist a physician in performing an ophthalmic surgery. The method includes receiving a quasi-real time image of at least a first portion of the eye. The at least the first portion of the eye includes an operating field for the ophthalmic surgery. A recommended next region and a recommended next procedure are determined based on the quasi-real time image and a computational model of the eye. An expected next result for the recommended next procedure is calculated using the quasi-real time image and the computational model. The recommended next region, the recommended next procedure and the expected result are provided to the physician.

According to the method and system disclosed herein, a physician may not only be provided with recommendations for next procedures but also the expected results for the next procedures. Consequently, a physician is better able to prepare for and perform surgery.

DETAILED DESCRIPTION OF THE PREFERRED EMBODIMENTS

Figure 1:
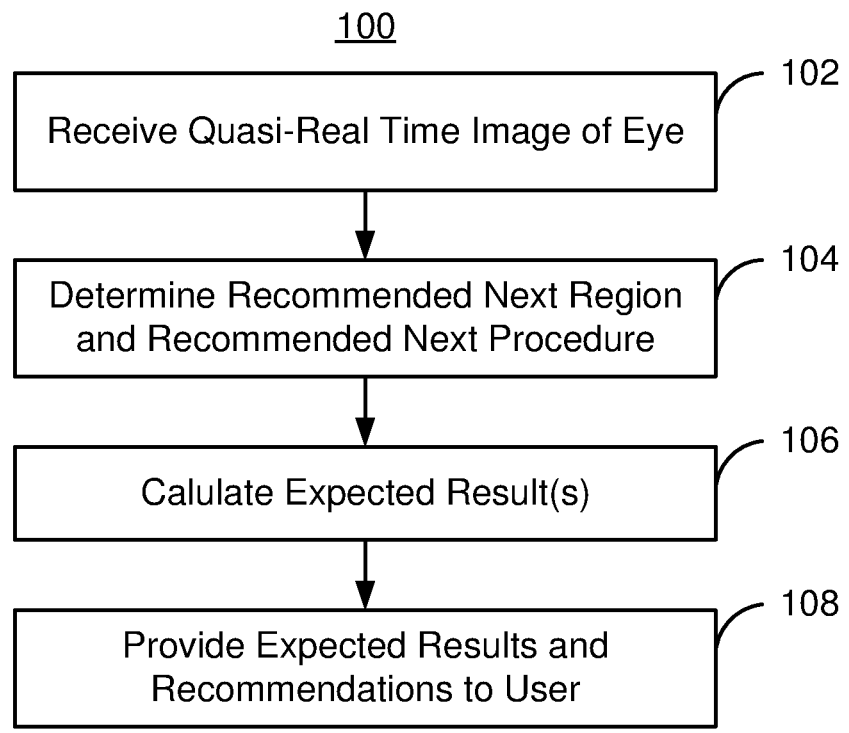
FIG. 1 is a flow chart depicting an exemplary embodiment of a method for assisting a physician during ophthalmic surgery using quasi-real time image(s).

The exemplary embodiments relate to mechanisms for assisting physicians during surgeries including ophthalmic surgery. The following description is presented to enable one of ordinary skill in the art to make and use the invention and is provided in the context of a patent application and its requirements. Various modifications to the exemplary embodiments and the generic principles and features described herein will be readily apparent. The exemplary embodiments are mainly described in terms of particular methods and systems provided in particular implementations. However, the methods and systems will operate effectively in other implementations. Phrases such as "exemplary embodiment", "one embodiment" and "another embodiment" may refer to the same or different embodiments as well as to multiple embodiments. The embodiments will be described with respect to systems and/or devices having certain components. However, the systems and/or devices may include more or less components than those shown, and variations in the arrangement and type of the components may be made without departing from the scope of the invention. Further, although specific blocks are depicted, various functions of the blocks may be separated into different blocks or combined. The exemplary embodiments will also be described in the context of particular methods having certain steps. However, the method and system operate effectively for other methods having different and/or additional steps and steps in different orders that are not inconsistent with the exemplary embodiments. Thus, the present invention is not intended to be limited to the embodiments shown, but is to be accorded the widest scope consistent with the principles and features described herein.

The method and system are also described in terms of singular items rather than plural items. For example, a quasi-real time image, a recommended next region, a recommended next procedure and an expected result are discussed. One of ordinary skill in the art will recognize that these singular terms encompass plural. For example, a quasi-real time image may include one or more quasi-real time images, an expected result may include one or more expected results, a recommended next procedure may include one or more procedures, a next procedure may include one or more next procedures and so on.

In certain embodiments, the system includes one or more processors and a memory. The one or more processors may be configured to execute instructions stored in the memory to cause and control the process set forth in the drawings and described below. As used herein, a processor may include one or more microprocessors, field-programmable gate arrays (FPGAs), controllers, or any other suitable computing devices or resources, and memory may take the form of volatile or non-volatile memory including, without limitation, magnetic media, optical media, random access memory (RAM), read-only memory (ROM), removable media, or any other suitable memory component. Memory may store instructions for programs and algorithms that, when executed by a processor, implement the functionality described herein with respect to any such processor, memory, or component that includes processing functionality. Further, aspects of the method and system may take the form of an entirely hardware embodiment, an entirely software embodiment (including firmware, resident software, micro-code, etc.) or an embodiment combining software and hardware aspects. Furthermore, aspects of the method and system may take the form of a software component(s) executed on at least one processor and which may be embodied in one or more computer readable medium(s) having computer readable program code embodied thereon.

A method and system assist a physician in performing an ophthalmic surgery. The method includes receiving a quasi-real time image of at least a first portion of the eye. This portion of the eye includes an operating field for the ophthalmic surgery. A recommended next region and a recommended next procedure are determined based on the quasi-real time image and a computational model of the eye. An expected next result for the recommended next procedure is calculated using the quasi-real time image and the computational model. The recommended next region, the recommended next procedure and the expected result are provided to the physician.

FIG. 1 is a flow chart depicting an exemplary embodiment of a method 100 for assisting a physician during ophthalmic surgery using quasi-real time image(s). For simplicity, some steps may be omitted, interleaved, performed in another order and/or combined. The method 100 may include executing instructions on one or more processors. Further, the method 100 is described in the context of ophthalmic surgery. However, the method 100 may be extended to other types of surgery.

At least one quasi-real time image of at least a portion of the eye is received, via step 102. Receipt of the image in step 102 may include receiving data for the image from a separate imaging system or capturing the image by a portion of the system carrying out the method 100. Step 102 need not include rendering the image for the physician. Instead, step 102 includes obtaining data for the eye. The quasi-real time image(s) are captured in situ. In other words, the quasi-real time image(s) are captured in the operating room. Further, quasi-real time images may include the entire eye or a portion of the eye. However, the operating field in which the physician desires to perform the next surgical procedure is shown in the quasi-real time image(s). The quasi-real time image(s) may include optical coherence tomograph(s) (OCTs), ultrasound image(s), high frequency ultrasound image(s), ultrasound biomicroscopy (UBM) image(s) and/or other image(s). Thus, as used herein, the term image may refer to a quantitative scan. Thus, the quasi-real time image may include the volume of the eye or simply a cross-section of the eye. In some embodiments, video or other mechanism for showing the progression of time may be part of the quasi-real time image(s) received in step 102. Further, the resolution of the imaging technique is sufficiently to allow the physician to view the relevant features of the eye within the operating field. The quasi-real time image is termed "quasi-real time" because the procedures used to capture the images are sufficiently fast to be performed during surgery. For example, in some embodiments, the image may be provided in not more than thirty minutes. In some such embodiments, capturing the image may be completed in not more than ten minutes. In some embodiments, capturing the quasi-real time image may require not more than one minute.

As used herein, capturing an image may include any focusing and/or other processes performed. For example, if the quasi-real time image(s) are desired to indicate stress concentrations, then step 102 may include obtaining multiple quasi-real time images using optical coherence tomography (OCT) at different intraocular pressures (IOPs) for the patient's eye. In some cases, an OCT image of the eye is acquired at each IOP. Different IOPs may result in different distortions for high stress regions than for low stress regions. Further, thinning or tearing of particular components of the eye may be better indicated at different IOPs. A single, concatenating image or model of the eye indicating the high and low stress regions may be formed as described below.

A recommended next region and a recommended next procedure are determined based on the quasi-real time image(s) and a computational model of the eye, via step 104. The computational model of the eye may include data that are specific to the patient as well as data characteristic of portions of eye. For example, the quasi-real time image(s) received in step 102 or a pre-operation image of the patient's eye may be used to determine sizes of various components of the eye and/or expected locations of features such as an ERM. Such data may be unique to the patient. The computational model may also include mechanical properties of the eye such as the tensile strength of certain tissue within the eye. Such data may be characteristic to the tissue across different patients. In some embodiments, a finite element analysis (FEM) model of the eye may be generated and used as the computational model of the eye.

As part of step 104, therefore, data for the quasi-real time image(s) received in step 102 are processed. For example, the stresses in particular regions may be determined from the distortions seen in the quasi-real time image data at various IOPs. Similarly, striations due to higher stress, fold marks, thinning, tears and/or other issues in various regions may be determined based on the data acquired and the computational model, which may indicate how an eye is expected to behave.

Determination of the recommended next region and next procedure in step 104 may include identifying regions of high stress or other issues within the operating fields. For example, step 104 may also include generating data for an arrow near tissue under higher stress and/or near thinned tissue. Step 104 may also include generating a visual model of the eye. For example, the one color (e.g. red) may be selected for high stress regions or regions near retinal tears and another color (e.g. blue) may be selected for lower stress regions. Thus, regions which are more problematic and/or are likely candidates for the next procedure are determined.

In some embodiments, step 104 may include explicitly determining a specific recommended procedure. However, in general, the recommended procedure is known for the particular operation underway. For example, for ERM removal, the next procedure is typically cutting a section of the ERM. Thus, highlighting a region of high stress may inherently indicate the next procedure (a cut).

An expected next result for the recommended next procedure is also calculated using the quasi-real time image and the computational model, via step 108. For example, for ERM removal, the next recommended procedure (a cut) at a particular, recommended region releases stress in that region. The procedure may also result in a release of the ERM in that location. Thus, step 108 includes using the computational model of the eye to determine the reaction of surrounding tissue to a release of stress in that region. For example, the ERM may be expected to move in a particular direction. Step 108 models this response.

The recommended next region, the recommended next procedure and the expected result are provided to the physician, via step 108. Portions of step 108 may be performed at different times. For example, the recommended next region and recommended next procedure may be performed by rendering the quasi-real time image or model that is generated in step 104. For example, an arrow may be placed near tissue under higher stress and/or near thinned tissue to indicate the recommended next region and/or procedure. Alternatively, the quasi-real time image may simply be rendered and shown to the physician to allow the physician to analyze the image. Step 108 may also include rendering the visual model of the eye generated in step 104. For example, the image may render high stress regions or regions near retinal tears in one color (e.g. red) and lower stress regions in another color (e.g. blue). Thus, regions which are more problematic and/or are likely candidates for the next procedure are indicated. The surgeon may be shown a model of the eye with particular high stress regions in a different color or otherwise indicated. Providing the expected result to the physician may be performed in response to input received. For example, if a particular recommended region is selected, then the expected result of performing the recommended procedure at that region (which was calculated in step 106) is provided in step 108. Step 108 may thus include rendering the model of the eye calculated in step 106.

Figure 2A:
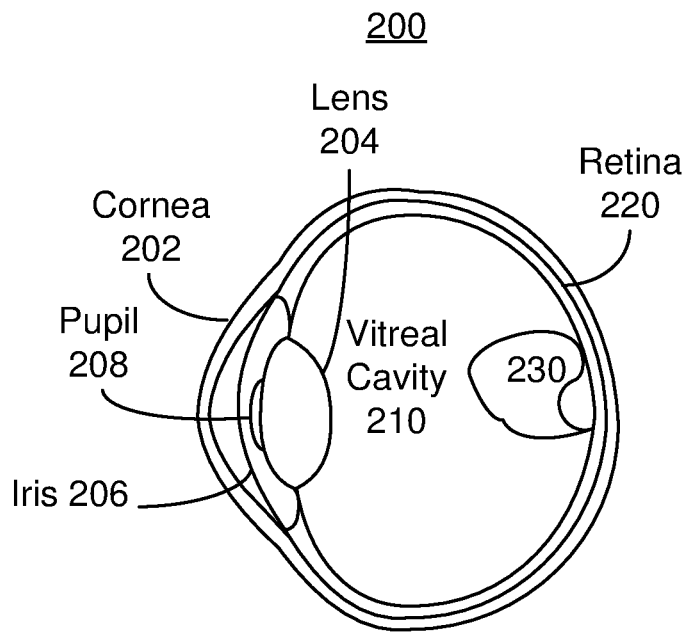
FIGS. 2A, 2B, 2C and 2D depict exemplary embodiments of quasi-real time images of the eye including recommendations and expected results of procedures.

The output of method 100 may be seen, for example, via FIGS. 2A-2D. FIGS. 2A, 2B, 2C and 2D depict exemplary embodiments of quasi-real time images and models of the eye 200 including recommendations and expected results of procedures. FIGS. 2A-2D are not to scale and for explanatory purposes only. Thus, a particular patient, condition or response is not intended to be shown in FIGS. 2A-2D. FIG. 2A depicts an image 200 of the eye. The cornea 202, lens 204, iris 206, pupil 208, vitreal cavity 210 and retina 220 are indicated for the purposes of explanation. Region 230 in the vitreal cavity 210 may be an ERM, a region of high stress or other issue. For the purposes of explanation, it is presumed that region 230 is an ERM 230. The image 200 may be or be part of a quasi-real time image taken just before or at some time during surgery. Alternatively, the image 200 may be a pre-operation image taken previously that happens to continue to represent the condition of the eye.

Figure 5:
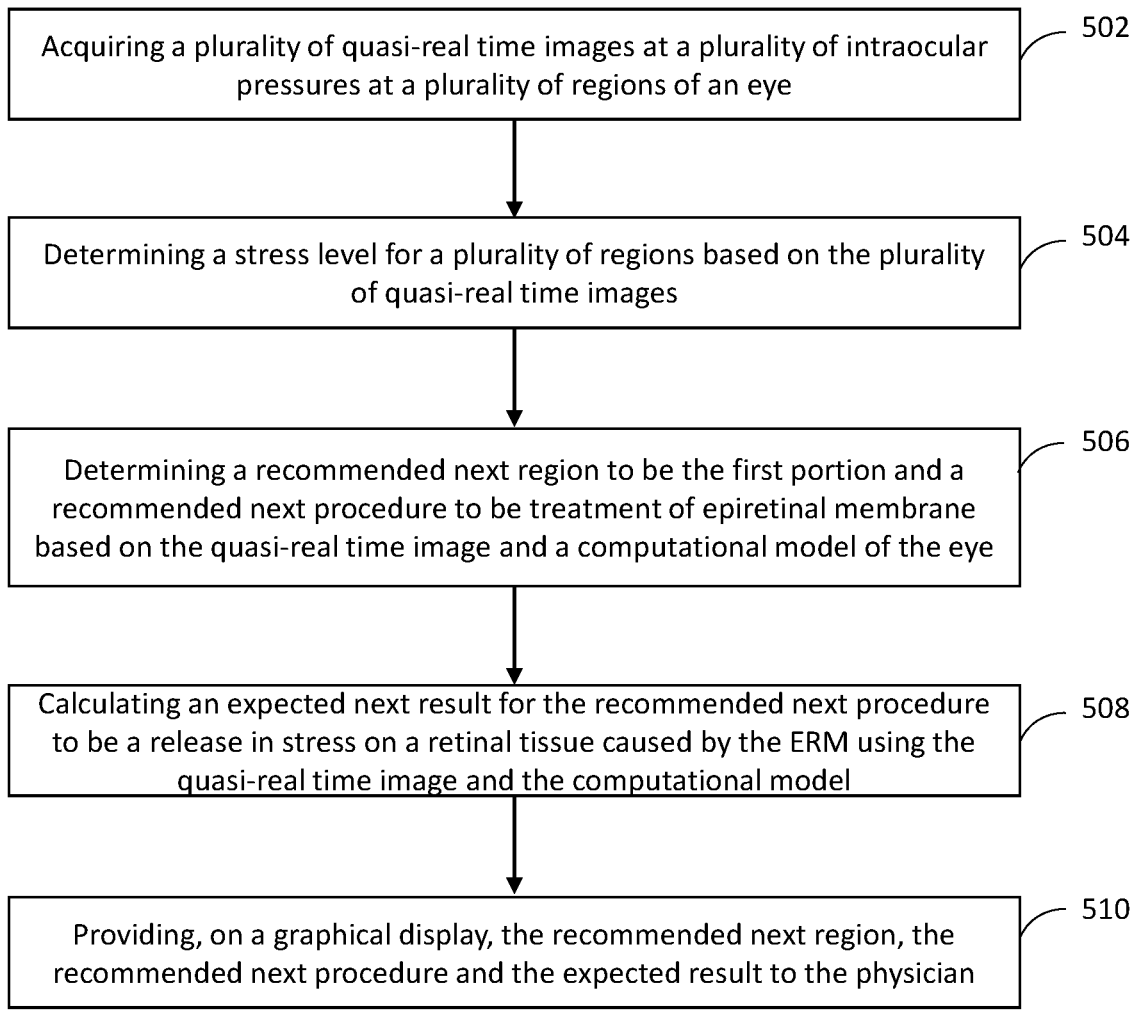
FIG. 5 is a flow chart depicting a method for assisting a physician during ophthalmic surgery according to some embodiments of the disclosed technology.

FIG. 5 is a flow chart depicting an embodiment of a method 500 for assisting a physician during ophthalmic surgery using quasi-real time image(s). The method 500 includes acquiring a plurality of quasi-real time images at a plurality of intraocular pressures at a plurality of regions of an eye 502. Using a plurality of intraocular pressures results in a varied degree in distortions in the plurality of quasi-real time images and an indication of a varied degree of stress concentrations in an eye tissue. Next, the method 500 involves determining a stress level for a plurality of regions based on the plurality of quasi-real time images 504. In some cases, a first portion of the plurality of regions has a higher stress than a second portion of the plurality of regions. Next, the method 500 involves determining a recommended next region to be the first portion and a recommended next procedure to be treatment of epiretinal membrane (ERM) based on the quasi-real time image and a computational model of the eye 506 and calculating an expected next result for the recommended next procedure to be a release in stress on a retinal tissue caused by the ERM using the quasi-real time image and the computational model 508. The method 500 also involves displaying, on a graphical display, the recommended next region, the recommended next procedure and the expected result to the physician 510.

Figure 2B:
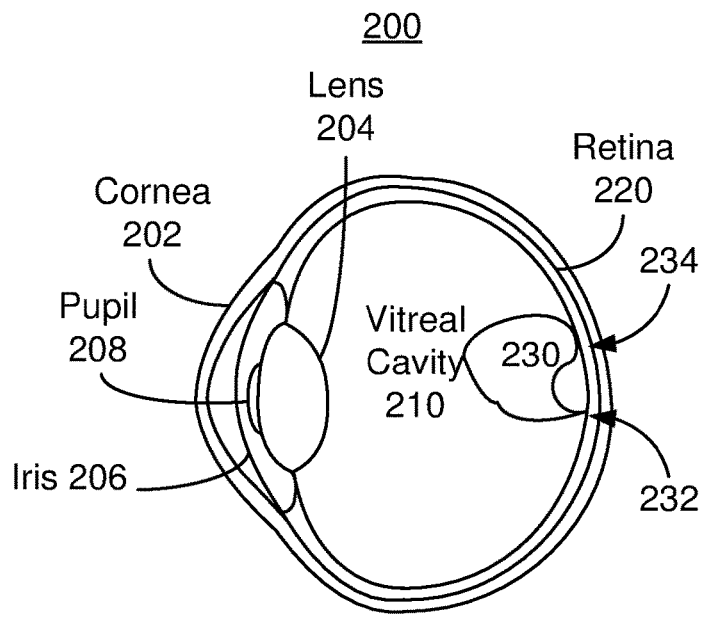

FIG. 2B depicts an image 200 of the eye with recommended regions 232 and 234 indicated by arrows. The recommended regions 232 and 234 may be high stress regions and/or regions where the ERM 230 is pulling on the retina 220. The image 200 may be purely a model or may be the image 200 shown in FIG. 2A with recommended regions 232 and 234 highlighted. Because the ERM 230 is to be removed, the recommended procedure (cutting the ERM 230) is inherently known. The image 200' may be rendered on a graphical display for the physician to view. In other embodiments, the recommendations may be provided in another manner.

Figure 2C:
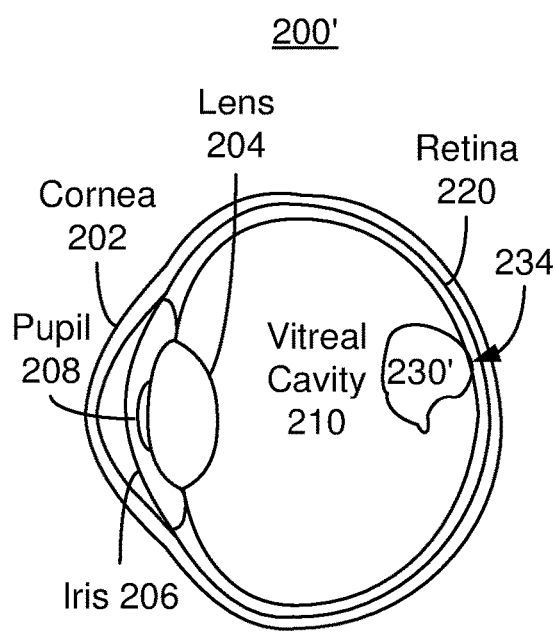
Figure 2D:
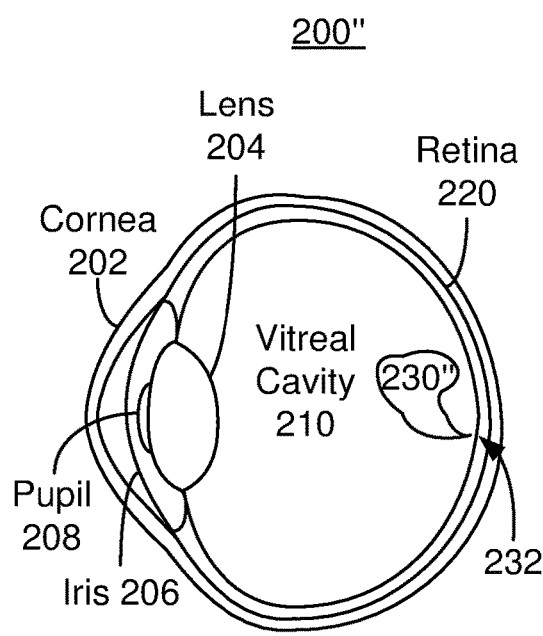

FIG. 2C depicts an image 200' or an expected result of the recommended procedure for recommended region 232 being carried out. Thus, the image 200' may be considered to be a model of the eye in the event that a cut is made at the region 232. As can be seen, the ERM 230' is modeled to shrink away from the region 232, change shape and rotate. Other changes in shape and/or position might be modeled for different stresses. The image 200' may be rendered on a graphical display for the physician to view in response to the physician selecting the region 232. In other embodiments, the expected result may be provided in another manner.

FIG. 2C depicts an image 200" or an expected result of the recommended procedure for the recommended region 234 being carried out. Thus, the image 200" may be considered to be a model of the eye in the event that a cut is made at the region 234. As can be seen, the ERM 230" is modeled to shrink away from the region 234, change shape and rotate. Other changes in shape and/or position might be modeled for different stresses. The image 200" may be rendered on a graphical display for the physician to view in response to the physician selecting the region 234. In other embodiments, the expected result may be provided in another manner.

Using the method 100, a surgeon may be better able to perform surgery on the eye. For example, just prior to surgery, the method 100 may be used to provide up-to-date information on the eye and indicate to the physician whether their surgical plan is still appropriate. If not, the surgeon may opt to proceed in a different manner. After one or more procedures (e.g. cuts) have been performed as part of the surgery, the method 100 may be repeated. Thus, the surgeon may determine whether the eye is responding as expected and may be able to adjust for deviations made to the surgical plan. The surgeon may also be able to have a general idea of how the eye is expected to respond prior to a particular procedure and be able to better select the appropriate option. The ability of the physician to carry out surgery is, therefore, improved. The method 100 may be particularly useful where the surgeon is presented with a situation that is very complex and/or has altered significantly since formation of the surgical plan. Thus, the method 100 may have particular utility for conditions, such as diabetic retinopathy or proliferative vitreoretinopathy, that progress relatively quickly and/or which present the surgeon with a complicated pathology. The ability of the physician to carry out surgery is, therefore, improved.

Figure 3:
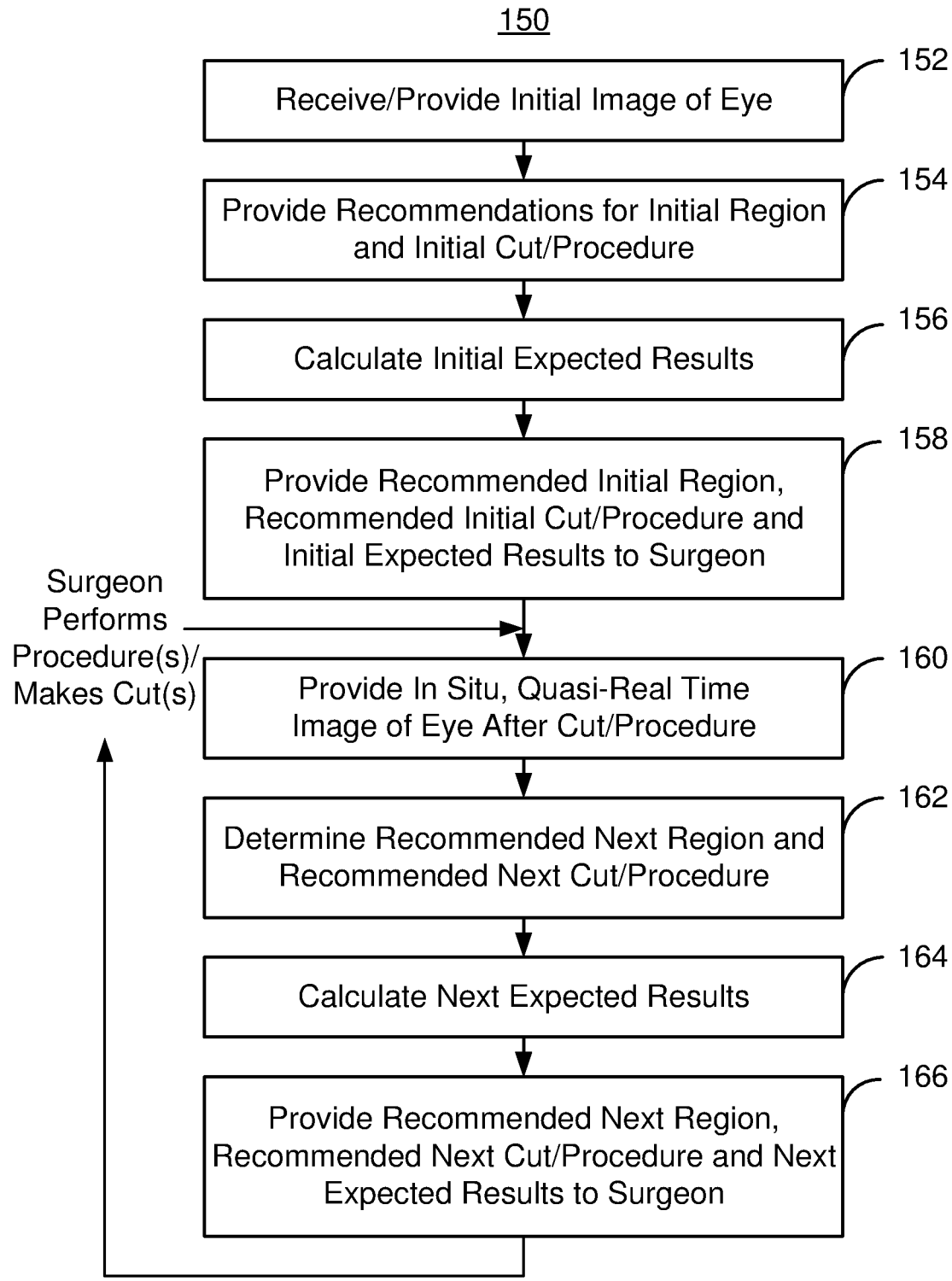
FIG. 3 is a flow chart depicting an exemplary embodiment of a method for assisting a physician during ophthalmic surgery using quasi-real time image(s).

FIG. 3 is a flow chart depicting an exemplary embodiment of a method 150 for assisting a physician during ophthalmic surgery using quasi-real time image(s). For simplicity, some steps may be omitted, interleaved, performed in another order and/or combined. The method 150 may include executing instructions on one or more processors. Further, the method 150 is described in the context of ophthalmic surgery. However, the method 150 may be extended to other types of surgery.

At least one initial image of at least a portion of the eye is received, via step 152. Receipt of the image in step 152 may include receiving data for the image from a separate imaging system or capturing the image by a portion of the system carrying out the method 150. Thus, the image received in step 152 may, but need not be a quasi-real time image. The image(s) received in step 152 may include OCTs, ultrasound image(s), high frequency ultrasound image(s), UBM image(s) and/or another three-dimensional image(s).

A recommended initial region and a recommended initial procedure are determined based on the initial image(s) and a computational model of the eye, via step 154. The computational model of the eye may be analogous the computational model discussed above for the method 100. As part of step 154, therefore, data for the initial image(s) received in step 152 are processed. For example, the stresses in particular regions may be determined from the distortions seen in the initial image data. Similarly, striations due to higher stress, fold marks, thinning, tears and/or other issues in various regions may be determined based on the image data and the computational model. Step 154 may be performed in a manner analogous to step 104, described above. However, the initial image, which may or may not be a quasi-real time image, is used. In some embodiments, step 154 may include explicitly determining a specific recommended procedure. However, in general, the recommended procedure is known for the particular operation underway.

An initial expected result for the initial procedure is calculated, via step 156. Step 156 may be analogous to step 106, described above. However, the initial image, which may or may not be a quasi-real time image, is used. The initial recommended region, the initial recommended procedure and the initial expected result may be provided, to the physician, via step 158. Step 158 is analogous to step 108. Thus, image(s) of the eye and/or a model of the eye may be displayed for the physician. In some embodiments, therefore, this information is provided graphically to the physician. In other embodiments, another mechanism for providing the initial recommended region, the initial recommended procedure and the initial expected result is used.

The surgeon may then perform one or more procedures, such as making cut(s). The surgeon may opt to take the recommendation(s) provided in step 158 or perform another procedure. For example, the surgeon may desire to make a cut at a different location. The surgeon may also perform multiple procedures.

After the surgeon has performed the procedure(s), at least one in situ, quasi-real time image of at least a portion of the eye is received, via step 160. Receipt of the image in step 160 may include receiving data for the image from a separate imaging system or capturing the image by a portion of the system carrying out the method 150. Step 160 need not include rendering the image for the physician. Instead, step 160 includes obtaining data for the eye. Step 160 is thus analogous to step 102.

A recommended next region and a recommended next procedure are determined based on the quasi-real time image(s) and a computational model of the eye, via step 162. Step 162 is analogous to step 104.

An expected next result for the recommended next procedure is also calculated using the quasi-real time image and the computational model, via step 164. Thus, step 164 includes using the computational model of the eye to determine the reaction of surrounding tissue to a release of stress in that region.

The recommended next region, the recommended next procedure and the expected result are provided to the physician, via step 166. Portions of step 166 may be performed at different times. For example, the recommended next region and recommended next procedure may be performed by rendering the quasi-real time image or model that is generated in step 162. Providing the expected result to the physician may be performed in response to input received. For example, if a particular recommended region is selected, then the expected result of performing the recommended procedure at that region is provided in step 166. Step 166 may thus include rendering the model of the eye calculated in step 164.

The surgeon may then be allowed to execute one or more other procedure(s). For example, one or more other cuts may be made. The physician can, but need not, follow the recommendations provided in the method 150. Step 160 may then be returned to and the eye rescanned. The recommendations for the next step and next region may be determined with the new scan and expected results of the new recommendations determined in step 164. These new recommendations and new expected results may be provided to the physician, via step 166. Thus, steps 160, 162, 164 and 166 may be iteratively repeated to assist the surgeon. These steps can, but need not, be repeated every time the surgeon performs a procedure. Alternatively, the steps 160, 162, 164 and 166 may be repeated at selected time(s) during the operation. Thus, the physician may opt to repeat these steps only when s/he deems it helpful or necessary.

Using the method 150, a surgeon may be better able to perform surgery on the eye. The method 150 may commence using the surgeon's previous information (a more dated initial image) and/or may use a quasi-real time image that is recently captured. Thus, the physician may determine whether their surgical plan is still appropriate. After one or more procedures have been performed as part of the surgery, the steps 160, 162, 164 and 166 may be carried out or repeated. Thus, the surgeon may determine whether the eye is responding as expected and may be able to adjust for their actions throughout surgery. The surgeon may also be able to have a general idea of how the eye is expected to respond prior to a particular procedure and be able to better select the appropriate option. Consequently, the ability of the physician to carry out ophthalmic surgery may be enhanced.

Figure 4:
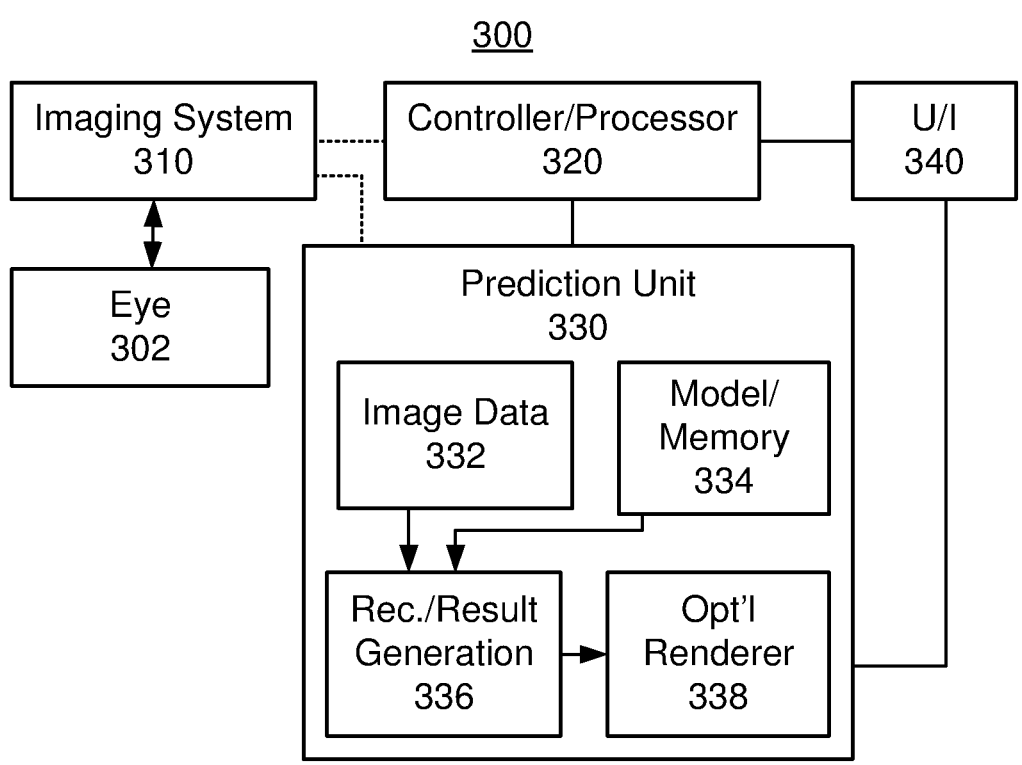
FIG. 4 is a block diagram of an exemplary embodiment of an apparatus for assisting a physician during ophthalmic surgery using quasi-real time image(s).

FIG. 4 is a block diagram of an exemplary embodiment of an apparatus 300 for assisting a physician during ophthalmic surgery using quasi-real time image(s). For simplicity, only some components are shown. In addition, the components depicted in FIG. 4 may be packaged together in a single apparatus such as an OCT or other imaging system. Alternatively, certain components, such as portions of data collection and processing, may be implemented separately. Further, the components may be implemented in hardware and, in some cases, software. Also shown in FIG. 4 is the sample eye 302 to be interrogated.

The apparatus 300 includes an imaging system 310, a controller/processor 320, a prediction unit 330 and a user interface (U/I) 340. The imaging system 310 may be separate from the remainder of the system 300. Consequently, the imaging system 310 is shown as connected by dashed lines. If part of the apparatus 300, the imaging system 310 may be is controlled by the processor 320. The operator may input instructions and receive output from the U/I 340. For example, the operator may set the regions of the eye 302 scanned by the imaging system 310, view results or otherwise provide instructions and receive output from the system 300. In some embodiments, the controller/processor 320 is linked with or controls a system that sets the IOP for the eye 302 or other features. Thus, the controller processor 320 may be used to control quasi-real time image capture.

The prediction unit 330 may be implemented at least in part in software. The prediction unit 330 processes data from the imaging system 310. Thus, image data 332 and computational model 334 of the eye are shown. Portions of the computational model 334 may be stored in memory and are indicated as such in FIG. 4. For example, values for the tensile strength or density of various portions of the eye 302 as well as parameters for the patient may be stored for the computational model 334. As such, an FEA model or other model of the eye may be generated and used. The recommendation/expected result generator 336 processes the image data 332 and uses the computational model 334 to determine the recommended region(s), recommended procedure(s) and expected result(s). Using the optional renderer 338, these may be graphically displayed to the physician on U/I 340. The optional renderer 338 may also be used to simply display the quasi-real time image data on the U/I 340. The apparatus 300 thus allows the eye 302 to be scanned and mapped during surgery, data for the eye to be processed and recommendations and expected responses of the eye 302 to be determined. Using the apparatus 300, therefore, the method 100 and/or 150 may be implemented. One or more of the benefits of the methods 100 and/or 150 may thus be achieved.

A method and system for assisting a surgeon, particularly for ophthalmic surgery, have been described. The method and systems have been described in accordance with the exemplary embodiments shown, and one of ordinary skill in the art will readily recognize that there could be variations to the embodiments, and any variations would be within the spirit and scope of the method and system. Accordingly, many modifications may be made by one of ordinary skill in the art without departing from the spirit and scope of the appended claims.

We claim:

1. A method for assisting a physician in performing an ophthalmic surgery comprising:
   a computational model generation step, comprising:
      setting an intraocular pressure of a patient's eye to a plurality of intraocular pressures;
      acquiring a plurality of quasi-real time images at the plurality of intraocular pressures at a plurality of regions of a retina of an eye, wherein the plurality of intraocular pressures results in a varied degree in distortions in the plurality of quasi-real time images and an indication of a varied degree of stress concentrations in the retina;
      determining a stress level for a plurality of regions based on the plurality of quasi-real time images, a first portion of the plurality of regions having a higher stress than a second portion of the plurality of regions; and
      generating a computational model of at least a portion of the patient's retinal tissue, the computational model including an indication of how the portion of the patient's retinal tissue will behave due to the stress levels for the plurality of regions; and a
   surgical recommendation step, comprising:
      iteratively determining a recommended next region to be the first portion and a recommended next procedure to be treatment of epiretinal membrane (ERM) based on the quasi-real time image and the computational model of the eye and calculating an expected next result for the recommended next procedure to be a release in stress on a retinal tissue caused by the ERM using the quasi-real time image and the computational model; and
      displaying, on a graphical display, the recommended next region, the recommended next procedure and the expected result to the physician.

2. The method of claim 1 further comprising:
   receiving an initial image of at least a second portion of the eye including the operating field, the initial image including an initial region for an initial procedure;
   calculating an initial expected result for the initial procedure using the initial image; and
   providing the initial expected result to the physician.

3. The method of claim 1 further comprising:
   iteratively repeating the receiving, determining, calculating and providing steps after the physician performs at least one procedure.

4. The method of claim 1 wherein the quasi-real time image includes at least one of an optical coherence tomograph, an ultrasound image, a high frequency ultrasound image, a ultrasound biomicroscopy (UBM) image and a three-dimensional image.

5. The method of claim 1 further comprising:
   capturing the plurality of quasi-real time images.

6. The method of claim 5 wherein the step of capturing the quasi-real time image takes not more than thirty minutes.

7. The method of claim 5 wherein the step of capturing the quasi-real time image takes not more than ten minutes.

8. The method of claim 5 wherein the step of capturing the quasi-real time image takes not more than one minute.

9. The method of claim 5 wherein the step of capturing the quasi-real time image further includes:
   indicating the first portion of the plurality of regions and the second portion of the plurality of regions.

10. The method of claim 1 wherein the computational model includes mechanical properties of retinal tissue of the eye.

11. The method of claim 1 wherein the recommended next procedure includes a recommended cut of the ERM.

12. A system for assisting a physician in performing ophthalmic surgery comprising:
   a controller configured to set an intraocular pressure of a patient's eye to a plurality of intraocular pressures;
   a quasi real-time image capture unit to acquire a plurality of quasi-real time images at a plurality of intraocular pressures at a plurality of regions of an eye, wherein the plurality of intraocular pressures results in a varied degree in distortions in the plurality of quasi-real time images and an indication of a varied degree of stress concentrations in the retina;

a predictive unit for:

determining a stress level for a plurality of regions based on the plurality of quasi-real time images, a first portion of the plurality of regions having a higher stress than a second portion of the plurality of regions;

generating a computational model of at least a portion of the patient's retinal tissue, the computational model including an indication of how the portion of the patient's retinal tissue will behave due to the stress levels for the plurality of regions; and iteratively determining a recommended next region to be the first portion and a recommended next procedure to be treatment of epiretinal membrane (ERM) based on the quasi-real time image and a computational model of the eye and calculating an expected next result for the recommended next procedure to be a release in stress on a retinal tissue caused by the ERM using the quasi-real time image and the computational model; and a user interface for displaying the recommended next region, the recommended next procedure and the expected result to the physician.

13. The system of claim 12 wherein the quasi-real time image capture unit also provides an initial image of at least a second portion of the eye including the operating field, the initial image including an initial region for an initial procedure; and the predictive unit further calculates an initial expected result for the initial procedure using the initial image and provides the initial expected result to the physician.

14. The system of claim 12 wherein the quasi-real time image includes at least one of an optical coherence tomograph, an ultrasound image, a high frequency ultrasound image, a ultrasound biomicroscopy (UBM) image and a three-dimensional image.

15. The system of claim 12 wherein the quasi-real time image is captured in not more than one minute.

16. The system of claim 12 wherein the computational model includes mechanical properties of retinal tissue of the eye.

* * * * *